United States Patent
Villard et al.

(10) Patent No.: US 9,100,025 B2
(45) Date of Patent: Aug. 4, 2015

(54) CIRCUIT FOR MEASURING THE RESONANT FREQUENCY OF NANORESONATORS

(71) Applicant: COMMISSARIAT A L'ENERGIE ATOMIQUE ET AUX ENERGIES ALTERNATIVES, Paris (FR)

(72) Inventors: Patrick Villard, Grenoble (FR); Gerard Billiot, St Nazaire les Eymes (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 0 days.

(21) Appl. No.: 14/253,709

(22) Filed: Apr. 15, 2014

(65) Prior Publication Data
US 2014/0312980 A1    Oct. 23, 2014

(30) Foreign Application Priority Data
Apr. 17, 2013  (FR) ...................... 13 53464

(51) Int. Cl.
*H03B 5/30* (2006.01)
*H03L 7/093* (2006.01)
(Continued)

(52) U.S. Cl.
CPC ............... *H03L 7/093* (2013.01); *B82Y 35/00* (2013.01); *G01G 3/16* (2013.01); *H03B 5/30* (2013.01); *H03L 7/02* (2013.01); *G01N 29/036* (2013.01); *G01N 29/22* (2013.01)

(58) Field of Classification Search
CPC ......... G01N 29/36; G01N 29/22; G01G 3/16; B82Y 35/00; H03B 5/30
USPC ............. 331/154, 96, 116 M, 2; 73/580, 579; 310/318
See application file for complete search history.

(56) References Cited

U.S. PATENT DOCUMENTS

| | | | |
|---|---|---|---|
| 2003/0033876 A1* | 2/2003 | Roukes et al. | ................... 73/580 |
| 2011/0254599 A1 | 10/2011 | Dikshit et al. | |
| 2013/0214644 A1 | 8/2013 | Hentz et al. | |

(Continued)

FOREIGN PATENT DOCUMENTS

| | | |
|---|---|---|
| FR | 2964651 A1 | 3/2012 |
| WO | 02090246 A2 | 11/2002 |
| WO | 2005081929 A2 | 9/2005 |

OTHER PUBLICATIONS

Chady Kharrat, et al., "Ha Loop Shaping Control for PLL-based Mechanical Resonance Tracking in NEMS Resonant Mass Sensors", 2008 IEEE Sensors, Oct. 26, 2008, pp. 1135-1138, IEEE, Piscataway, NJ, USA, XP031375279.

*Primary Examiner* — Arnold Kinkead
(74) *Attorney, Agent, or Firm* — Baker & Hostetler LLP (57) ABSTRACT

In the field of nanoresonator oscillators or NEMS (nanoelectromechanical systems) oscillators, a circuit is proposed for measuring the oscillation frequency of a resonator, including a phase-locked loop with a frequency-controlled oscillator and a phase comparator. The resonator includes a vibration excitation input and a dynamic polarization input (using strain gauges). The frequency-controlled oscillator applies a polarization frequency f1 to the polarization input. A frequency generator supplies a fixed intermediate frequency FI; a mixer receives the frequencies f1 and FI for producing an excitation frequency f0 that is the sum or difference of f1 and FI. The phase comparator receives the frequency FI and the output signal of the resonator and produces a control signal that is sent to the frequency-controlled oscillator, indirectly locking the oscillation frequency onto the resonant frequency of the resonator.

19 Claims, 8 Drawing Sheets

(51) Int. Cl.
*B82Y 35/00* (2011.01)
*G01G 3/16* (2006.01)
*H03L 7/02* (2006.01)
*G01N 29/22* (2006.01)
*G01N 29/036* (2006.01)

(56) References Cited

U.S. PATENT DOCUMENTS

2014/0055203 A1* 2/2014 Villard .......................... 331/25
2014/0182361 A1* 7/2014 Bargatin et al. ............. 73/61.79

* cited by examiner

CIRCUIT FOR MEASURING THE RESONANT FREQUENCY OF NANORESONATORS

CROSS-REFERENCE TO RELATED APPLICATION

This application claims priority to foreign French patent application No. FR 1353464, filed on Apr. 17, 2013, the disclosure of which is incorporated by reference in its entirety.

FIELD OF THE INVENTION

The invention relates to circuits with micro-machined electromechanical resonators and in particular to nanoresonator oscillators or NEMS (nanoelectromechanical systems) oscillators. These systems integrate, on one substrate, mechanical elements, micromachined to nanometer scale by collective microelectronics fabrication technologies.

These circuits can be used notably for measuring very small weights, typically between $10^{-24}$ and $10^{-21}$ grams. The applications targeted are, for example, gas analysis or mass spectrometry.

BACKGROUND

In such systems that use resonators, the signal to be measured is the resonant frequency of the nanoresonator, in fact depending directly on the weight of matter deposited on the resonator or adsorbed at its surface, a greater weight generating a lower resonant frequency.

Figure 1:
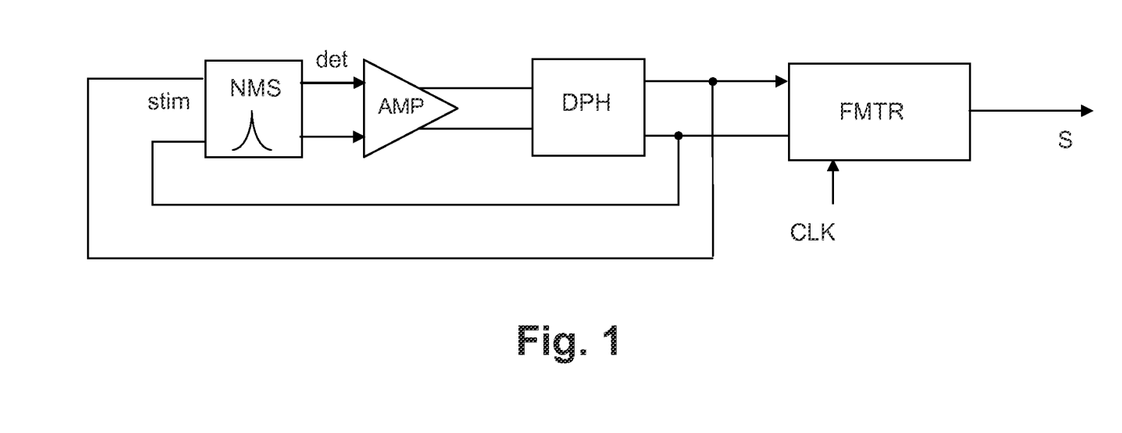
FIG. 1, already described, represents a self-oscillating measurement circuit with nanoresonator.

To measure the resonant frequency, it has already been proposed to use a self-oscillating circuit comprising a closed oscillation loop incorporating the resonator. FIG. 1 schematically represents such a self-oscillating circuit. The self-oscillating loop comprises the resonator NMS in series with an amplification and phase shifting subsystem, and a feedback between the output of the subsystem and an excitation input of the resonator. The amplification subsystem adds a gain by an amplifier AMP and a phase shift by a phase shifter DPH; it makes it possible to ensure natural oscillation conditions (open loop gain greater than or equal in modulus to 1 for a loop phase shift that is a multiple of $2\pi$). The oscillation frequency is the natural mechanical resonant frequency of the resonator NMS. It is measured at the output of the amplification subsystem by a frequency meter FMTR. The latter can operate, for example, on the principle of counting pulses of a reference clock CLK that has a frequency very much greater than the oscillation frequency. The analogue or digital output S of the frequency meter supplies a measurement of the resonator's own natural resonant frequency. This solution makes it possible to produce circuits with little bulk, which is important notably in the case where the aim is to produce a network comprising a large number of nanoresonators. However, since there is a wide technological dispersion in the resonators and the components of the amplification subsystem, it is difficult to guarantee a priori that gain and phase conditions will be obtained that allow for a spontaneous natural oscillation at the resonant frequency.

Figure 2:
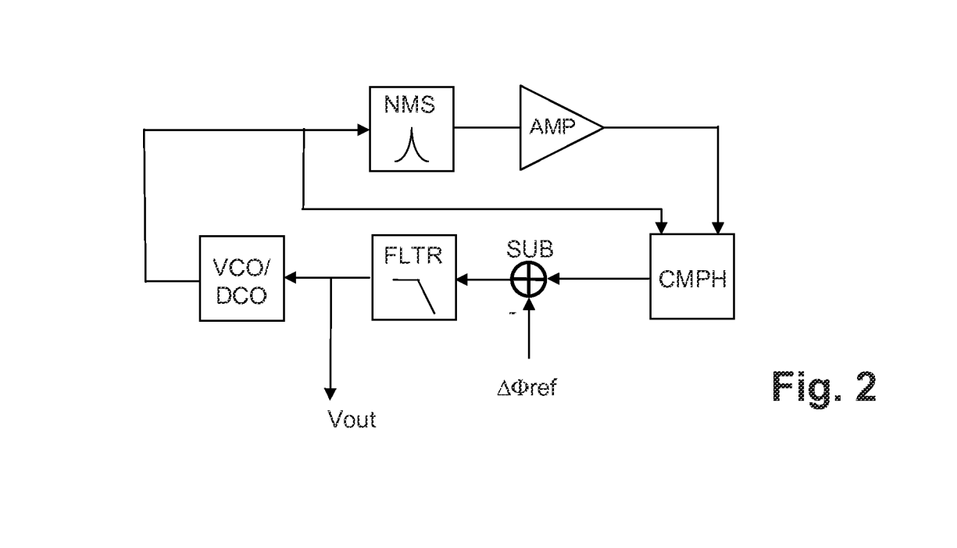
FIG. 2, already described, represents a nanoresonator oscillating measurement circuit, including a phase-locked loop.

Phase-locked loop (PLL loop) circuits have also been proposed, such as the one schematically represented in FIG. 2. The circuit also comprises a nanoresonator NMS in series with an amplifier AMP, a voltage-controlled oscillator (VCO) or a digitally-controlled oscillator (DCO) for exciting the resonator (NMS), a phase comparator CMPH, and a subtractor SUB for subtracting from the output of the phase comparator a value (modulo $2\pi$) which represents the natural phase shift $\Delta\Phi ref$ introduced by the resonator and the amplifier at the resonant frequency. A low-pass filter FLTR is inserted between the output of the phase comparator and a control input of the oscillator to ensure the stability of the locked loop.

The value $\Delta\Phi ref$ is a phase shift value measured by calibration by having the resonator and the amplifier operate in open loop mode at the resonant frequency and by observing the phase shift between the excitation signal of the resonator and the output of the amplifier.

The circuit is automatically locked onto the frequency for which the phase shift between the inputs of the phase comparator is equal to $\Delta\Phi ref$; this frequency is the natural resonant frequency of the resonator. In practice, in closed loop mode, the output of the phase comparator represents the phase shift of the resonator and of the amplifier. If it is not equal to $\Delta\Phi ref$, the control voltage of the oscillator VCO is adjusted until it becomes equal to $\Delta\Phi ref$, the phase shift corresponding to resonance. The measurement of the resonant frequency is then done by measuring the control voltage Vout of the oscillator, this voltage representing the oscillation frequency of the oscillator. This solution with PLL loop requires a preliminary calibration to know the phase shift $\Delta\Phi ref$ at resonance so that the latching of the loop does indeed correspond to the resonant frequency.

When the NEMS resonator is a resonator with electrostatic actuation and detection by piezoresistive gauges, it comprises two actuation electrodes that receive a signal at an actuation frequency f0 close to the resonant frequency. It has already been proposed that the detection gauges be powered by a dynamic polarization signal Vbias including an AC component with a frequency f1. The vibrating element of the resonator, for example a vibrating cantilever, vibrates at the frequency f0 and the piezoresistive gauges supply a detection signal at the frequency f0 but this signal includes a modulation component at the frequency f1 due to the polarization, which means that the output signal of the gauges comprises a component at a frequency f0−f1 and a component at the frequency f0+f1. One can be eliminated by filtering and the other carries phase shift information introduced by the resonator, a phase shift that is used for locking.

The patent publication WO2005/081929 describes an embodiment of this principle, with a generation of the signals at frequencies f0 and f1 by independent sources. A difference frequency f0−f1 is obtained by mixing and is used as a reference to detect the modulation of the output signal of the resonator, a signal which exactly comprises a component with frequency f0−f1. The correlation that exists between the frequency f0−f1 produced in the resonator and the reference frequency f0−f1 allows a measurement with a low phase noise. However, the embodiment described is hard to implement because it requires two frequency synthesizers to establish the frequencies f0 and f1, and these two synthesizers must be frequency-adjustable with a high resolution, one because it ensures the locking of the excitation of the resonator, the other because it must be adjusted if one wishes for the synchronous detection at the resonator output to be achieved at a constant frequency. The result thereof is bulk on the surface of the integrated circuit and corresponding costs and, also, high energy consumption.

SUMMARY OF THE INVENTION

One aim of the invention is to propose a resonator circuit reducing the necessary energy and power consumption resources, while preserving low phase noise.

According to the invention, a circuit is proposed for measuring the oscillation frequency of a resonator of the type including an excitation input for receiving an actuation signal at a frequency close to the resonant frequency of the resonator and a polarization input for receiving a polarization signal comprising an AC component at a polarization frequency f1, the circuit including a phase-locked loop comprising the resonator, a frequency-controlled oscillator, and a phase comparator, the measurement circuit being characterized in that the frequency-controlled oscillator produces the polarization frequency f1 and is linked to the polarization input of the resonator for applying this frequency f1 to it, and in that it furthermore comprises a frequency generator supplying a fixed intermediate frequency FI, a mixer for mixing the intermediate frequency and the polarization frequency f1 to establish an excitation frequency f0 that is the sum or difference of f1 and FI and for applying this excitation frequency f0 to the excitation input as actuation signal, the phase comparator receiving the intermediate frequency FI from the generator and a filtered output signal coming from the resonator, and supplying a locking signal serving to control the frequency f1 of the oscillator in a direction tending to maintain the excitation frequency at the output of the mixer at the value of the resonant frequency of the resonator.

The output of the mixer can be applied directly to the excitation input of the resonator, without prior pass-band filtering, the resonator itself providing, by its physical design, the pass-band filtering eliminating a single one of the two frequency components FI−f1 or FI+f1 present at the mixer output.

Consequently, the frequency-controlled oscillator of the phase-locked loop does not operate at the excitation frequency f0 as usual but at the polarization frequency f1. Apart from the resonator, the phase-locked loop comprises the frequency-controlled oscillator and the phase comparator, a mixer that produces the excitation frequency based on the intermediate frequency and the output of the frequency-controlled oscillator.

The intermediate frequency FI is fixed: it can be configurable to be able to be adjusted as a function of the characteristics of the resonator, but it does not vary due to the locking.

The term "frequency-controlled oscillator" refers as much to analogue oscillators, controlled by a voltage or by a digital input, as to direct digital frequency synthesizers supplying a sinusoidal signal of controlled phase and frequency.

The frequency generator that produces the intermediate frequency FI can supply a sinusoidal signal at frequency FI, which is favourable to the spectral purity of the signals generated by the mixer and of the signals produced by the resonator. In this case it will preferably be produced in the form of a direct digital frequency synthesizer, comprising an output digital-to-analogue converter. But it can also be envisaged for the frequency generator to supply square signals. It is less favourable from the point of view of spectral purity, since a square signal includes many harmonics, but it is far simpler to produce. It is in fact possible to use a simple clock circuit as frequency generator.

Whether the generator supplies square signals or sinusoidal signals, it can be proposed that it supplies two signals in phase quadrature (I and Q). The phase comparator receives the signals from the intermediate frequency generator and also works on two phase quadrature paths. It establishes two signals representing the phase differences observed on the two paths, between the output phase of the resonator and the I or Q phase of the frequency generator FI. These two signals are converted into a signal of phase shift value of which the amplitude represents the observed phase shift, a signal that serves to control the frequency-controlled oscillator. If the intermediate frequency generator FI is produced in the form of a clock circuit supplying square signals, it will be noted that it is very easy to produce two signals in phase quadrature starting from a basic clock of frequency four times equal to FI.

The frequency-controlled oscillator can, itself, supply signals in phase quadrature. The mixer present in the locked loop is then a complex mixer mixing the two paths of the frequency-controlled oscillator and the two paths of the intermediate frequency generator. Preferably, the mixer is used as a complex mixer in an open-loop calibration phase, i.e. it mixes the signals of paths I and Q, but it is used as a simple mixer in a closed-loop use phase. The calibration has the aim of determining the natural phase shift introduced by the resonator at the resonance: it consists in searching for the resonance by measuring the gain in open loop at a variable frequency, and in measuring the phase shift produced by the loop at the resonant frequency (the phase shift introduced by the resonator varies a lot near resonance). The phase shift at resonance is then introduced as setpoint into the closed locked loop.

Moreover, it can be proposed that the polarization frequency f1 is obtained by mixing a fixed frequency f2 (configurable as a function of the resonator type) and of a variable locked frequency f'1; in other words, the frequency-controlled oscillator that produces the frequency f1 comprises analogue or digital means (frequency-controlled oscillator or frequency synthesizer) for establishing a variable frequency f'1 under the control of the phase-locked loop, and a mixer for mixing this frequency f'1 with a fixed frequency f2 and thus producing the variable polarization frequency f1 (equal to f2+f'1 or f2−f'1). The adjustment of the frequency f1 is then done only by adjustment of the frequency f'1, which can be much lower than f1.

The phase comparison is preferably done with a completely digital circuit, an analogue-to-digital converter then being placed at the output of the resonator or preferably at the output of a low-pass filter that follows the resonator. However, the phase comparison could also be done in analogue.

BRIEF DESCRIPTION OF DRAWINGS

Other features and advantages of the invention will become apparent on reading the following detailed description which is given with reference to the appended drawings in which.

DETAILED DESCRIPTION

The nanoresonator used in the measurement circuit according to the invention is of the following type, whatever its practical embodiment: it possesses a vibration excitation input for receiving an actuation signal at an excitation frequency (f0), a polarization input for receiving a polarization signal having an AC component at a polarization frequency (f1), and finally an output for supplying an electrical signal representing the vibration of the nanoresonator. The polarization frequency serves to modulate the output signal to facilitate the measurement. The output signal, modulated by the polarization signal, comprises a component at an intermediate frequency which is the difference between the excitation frequency and the polarization frequency, as well as a component at a frequency that is the sum of these two frequencies. It is to this type of nanoresonator that the present invention generally applies. The component at the sum frequency will be eliminated by filtering. The component at the intermediate frequency contains an item of phase information that will be made use of in a phase-locked loop.

In an example that will be referred to in the remainder of the text, the micromachined nanoresonator is an electrostatic actuation and piezoresistive detection resonator, i.e. in practice a form of detection using strain gauges. Resonators of this type are described in the French patent FR2964651, for example. They comprise, for example, a vibrating cantilever suspended by one or more flexure arms; the vibration of the cantilever is excited and maintained by the electrostatic forces generated by electrodes receiving an AC electrical actuation signal at a frequency close to the mechanical resonant frequency of the cantilever; strain gauges, preferably piezoresistive gauges, are placed on the cantilever or on the flexure arms or on any mechanical element linked to the cantilever and reacting to the movements of the latter; they serve to detect the movement of the cantilever by detecting the strains that are exerted on them during the vibration of the cantilever. The strain gauges receive the polarization signal and supply the output signal of the nanoresonator.

Figure 3:
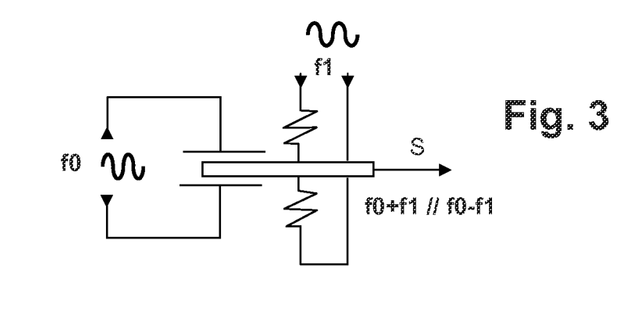
FIG. 3 symbolically represents a nanoresonator with detection by resistive gauges.

FIG. 3 symbolically represents the nanoresonator with its excitation input at a frequency f0, linked to actuation electrodes that excite the vibration of the cantilever, its polarization input at frequency f1, linked to the strain gauges, and its output S also linked to the strain gauges. The strain gauges are represented as resistances.

Figure 4:
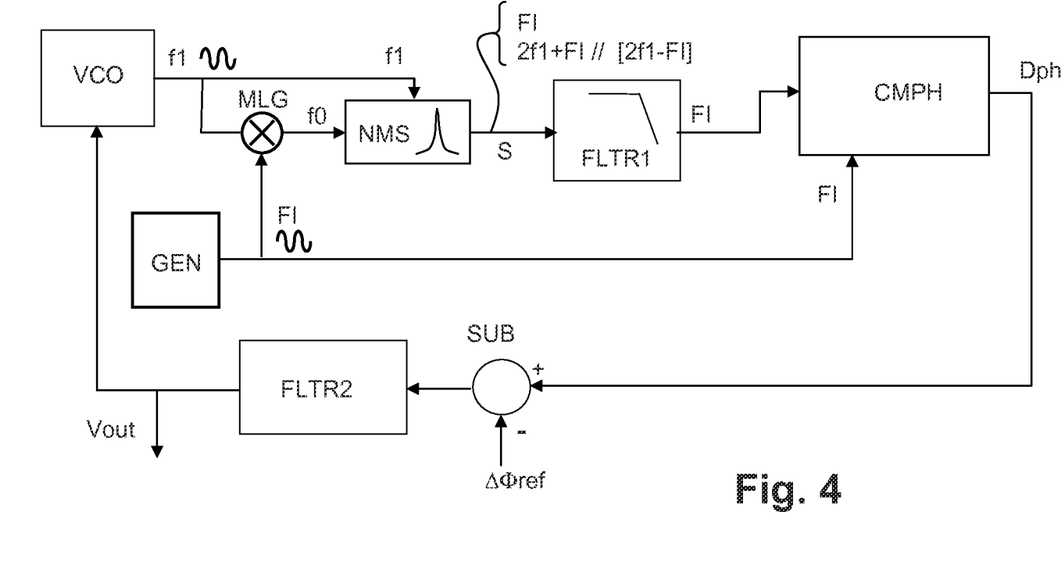
FIG. 4 represents a phase-locked loop measurement circuit in a simple version according to the invention.

The circuit for measuring the resonant frequency of the nanoresonator NMS is represented in FIG. 4. It uses a frequency-controlled oscillator VCO that produces a sinusoidal signal at a polarization frequency f1, and not a signal at the excitation frequency f0 as is the case in the prior art. This signal is applied to the polarization input of the nanoresonator. The polarization frequency f1 is therefore now a frequency that can vary as a function of the locking. The oscillator VCO can be an analogue oscillator controlled by a voltage or by a digital input, or a direct digital frequency synthesizer with controlled frequency.

According to the invention, a fixed-frequency frequency generator GEN is proposed that produces an intermediate frequency FI that is a reference frequency and not a frequency depending on the phase lock. A fixed-frequency generator is significantly simpler to produce than a controllable-frequency generator. In the example in FIG. 4, the generator produces a sinusoidal signal, but it will be seen that it can produce a square signal. A mixer MLG receives the fixed frequency FI from this generator as well as the output frequency f1 of the oscillator VCO. The mixer output contains a component at the sum frequency f1+FI and a component at the difference frequency f1−FI.

One of the components can be eliminated in a natural manner because the nanoresonator has by nature a very narrow pass-band; the frequency FI is chosen preferably higher than the bandwidth of the resonator so that one of the frequencies FI+f1 and f1−FI falls within the pass-band of the resonator, but not the other. For example, it is the component at the difference frequency f1−FI that is outside the band of the resonator and the frequency f1−FI that is inside the band of the resonator. In the remainder of the text it is considered that it is the frequency f1+FI which is inside the band of the resonator and which becomes the excitation frequency of the resonator, which is locked onto the resonator's own resonant frequency f0 owing to the phase-locked loop. The frequency f1−FI is then naturally eliminated by the resonator itself.

The nanoresonator excited by the frequency f1+FI and polarized by the frequency f1 supplies at its output a modulated signal having a component at a frequency FI and a component at a frequency 2f1+FI. The latter is eliminated by low-pass filtering in a filter FLTR1. The filter FLTR1 can comprise a low-noise amplifier if necessary. The component at frequency FI includes an item of phase information, the phase shift introduced by the resonator being very variable as a function of the offset between the excitation frequency f1+FI and the resonator's own resonant frequency f0. This item of phase information is detected in a phase comparator CMPH which receives on the one hand the original fixed intermediate frequency FI coming from the generator GEN and on the other hand the output of the filter FLTR1.

The phase comparator CMPH supplies a baseband signal, which represents a phase shift value Dph between the frequency FI supplied by the generator and the frequency FI coming from the filter FLTR1. This phase shift value is the variable onto which the oscillator VCO will be locked to return this variable to a setpoint value corresponding to resonance. The lock adjusts the frequency of the signal f1 so that the excitation signal at frequency FI+f1 has itself the frequency corresponding exactly to the resonance of the nanoresonator. The loop phase shift and the resonant frequency are determined by open-loop calibration and make it possible to define a phase setpoint to be complied with in order to be sure that a resonance situation exists. In closed loop, the setpoint is applied in the form of a phase shift value ΔΦref to an input of a subtractor SUB, which moreover receives the phase shift value Dph determined by the phase comparator. The subtractor output is filtered by a filter FTLR2 depending on the more or less sophisticated filtering functions with which one might wish to equip the lock to ensure its stability; the filtered output is applied as a control signal Vout to the controlled oscillator VCO. The control signal Vout is at the same time the output of the measurement circuit: it directly represents the value of the resonant frequency of the nanoresonator when the locked loop is in operation. The output is analogue or digital according to the design of the loop.

In the previous text, the output frequency FI of the generator is fixed. However, the fixed frequency can be configurable, i.e. it is possible to choose one fixed frequency or another according to the resonator or the type of resonator used.

As examples of frequencies, the nanoresonator can have a resonant frequency of 10 to 100 MHz, with a pass-band of a few kilohertz to a few tens of kilohertz. The intermediate frequency can be in the order of 20 to 100 kilohertz, the preferred condition being that the sum frequency f1–FI and the difference frequency f1–FI do not both fall within the pass-band of the resonator.

Generally, it is necessary to consider that the nanoresonator receives a sinusoidal analogue signal on its polarization input and that it supplies an analogue signal on its output. The filter FTLR1 that follows it can be analogue. All the rest of the phase-locked loop can be either digital, or analogue, or mixed. When the phase comparator is digital, an analogue-to-digital converter is needed between the output of the resonator and the input of the phase comparator. This converter is preferably placed at the output of the filter FLTR1. The filter FLTR1 can comprise a low-noise amplifier not represented, which amplifies the signal coming from the resonator before filtering it.

The frequency-controlled oscillator VCO can have an analogue or digital control; it can be produced in a purely analogue manner (oscillator with frequency controlled by a voltage) or in a partly digital form (analogue oscillator with frequency controlled by a digital data item) or almost totally digital (digitally-controlled frequency synthesizer followed by a digital-to-analogue converter supplying a waveform that is as sinusoidal as possible). The following figures give examples of these possibilities.

Figure 5:
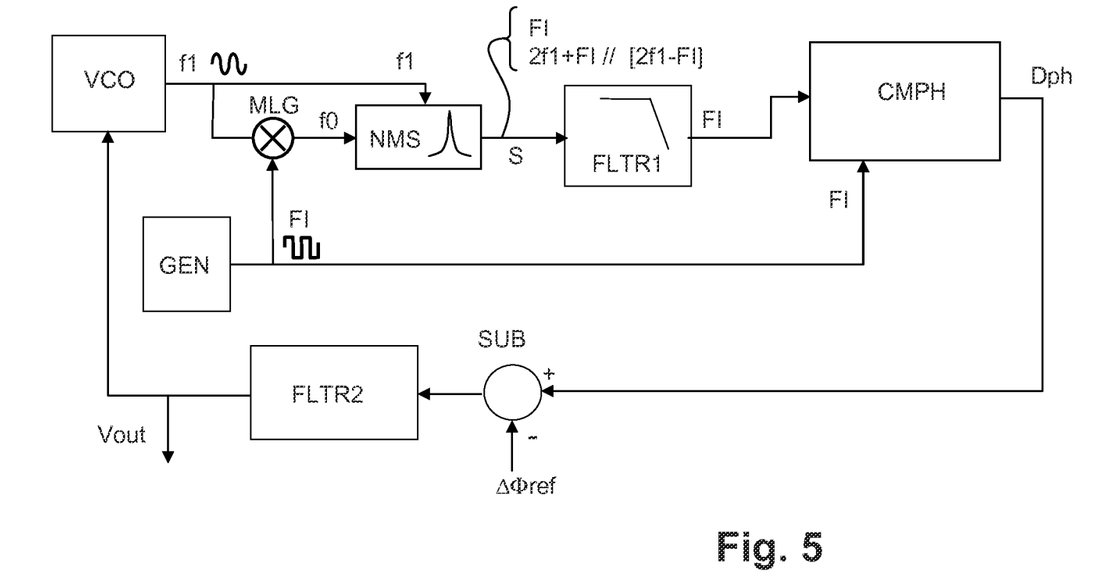
FIG. 5 represents an embodiment in which the excitation frequency of the resonator is produced from a square intermediate frequency signal.

FIG. 5 represents an embodiment in which the frequency generator FI is a simple clock circuit HOR supplying a square signal rather than a sinusoidal signal at the frequency FI.

This makes it possible to produce a particularly simple digital generator, using only logic functions such as a clock and flip-flops, but no digital-to-analogue converter. If the generator had to supply a sinusoidal signal and was made in the form of a direct digital frequency synthesizer, it would have to comprise such a digital-to-analogue converter to produce a roughly sinusoidal signal at the digitally synthesized frequency.

If the generator supplies a square signal at the frequency FI, this signal includes harmonics at the frequency multiples of FI. The output signal of the mixer therefore contains components at frequencies resulting from the combination of the frequency f1 with these harmonics. But the resonator is itself a filter with a very narrow band which eliminates most of these harmonics, so that the output signal is almost unaffected by the fact that the generator signal is square.

An advantage of a square output generator, apart from the fact that it is very simple to produce, is the fact that is can very easily supply two components in phase quadrature: it is enough that it be produced on the basis of a digital clock with a frequency quadruple that of the frequency FI. It will be seen further on that it is advantageous to provide a phase comparison of two paths in phase quadrature, and a frequency generator supplying a square signal is particularly advantageous in this case.

Figure 6:
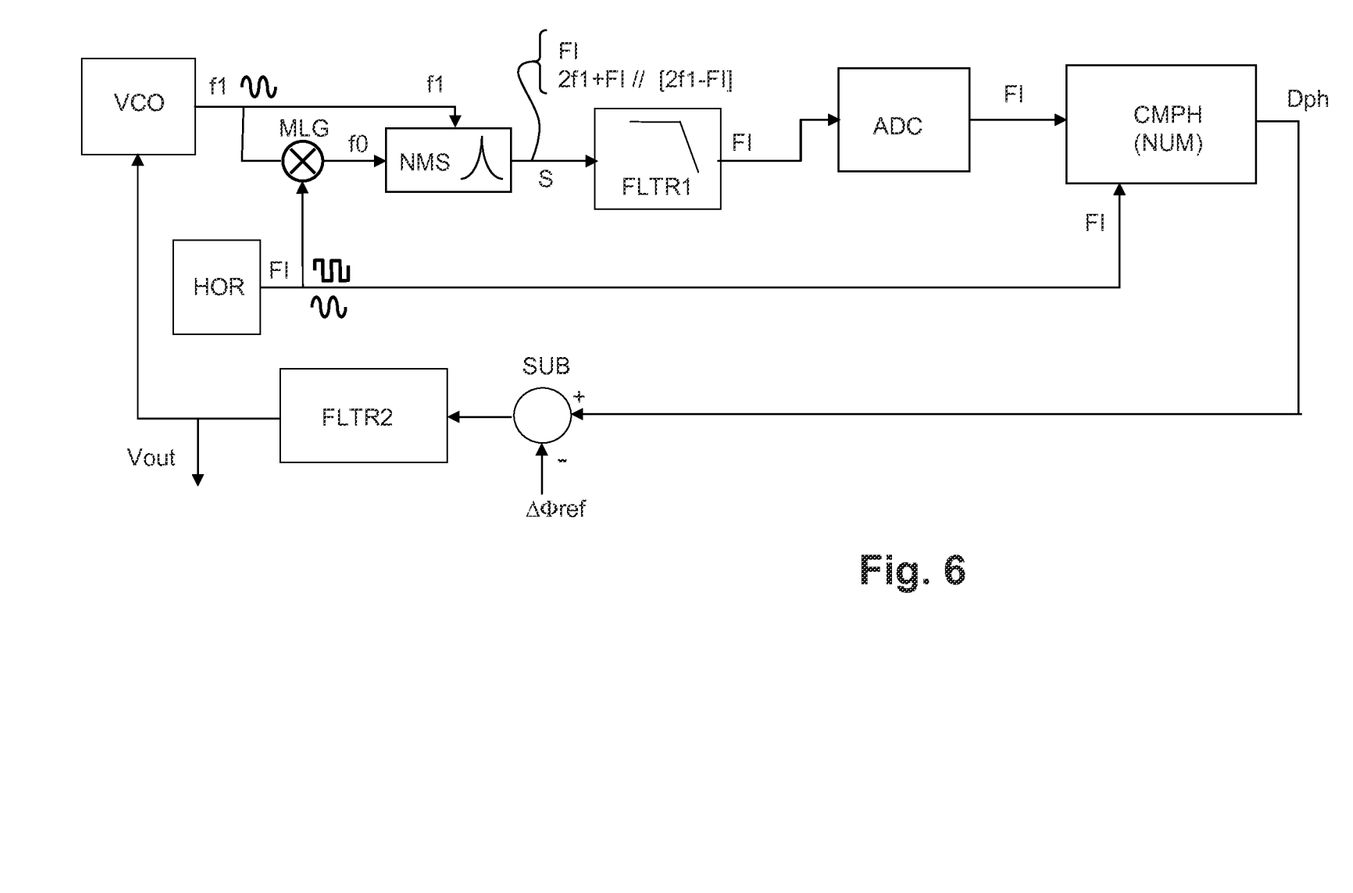
FIG. 6 represents a measurement circuit in which the phase comparator is digital.

FIG. 6 represents an embodiment in which the phase comparator is entirely digital. An analogue-to-digital converter ADC is provided upstream of the comparator, placed at the output of the filter FLTR1; it converts a signal at frequency FI and supplies a digital signal at frequency FI having the phase and the frequency of the signal at the resonator output.

Figure 7:
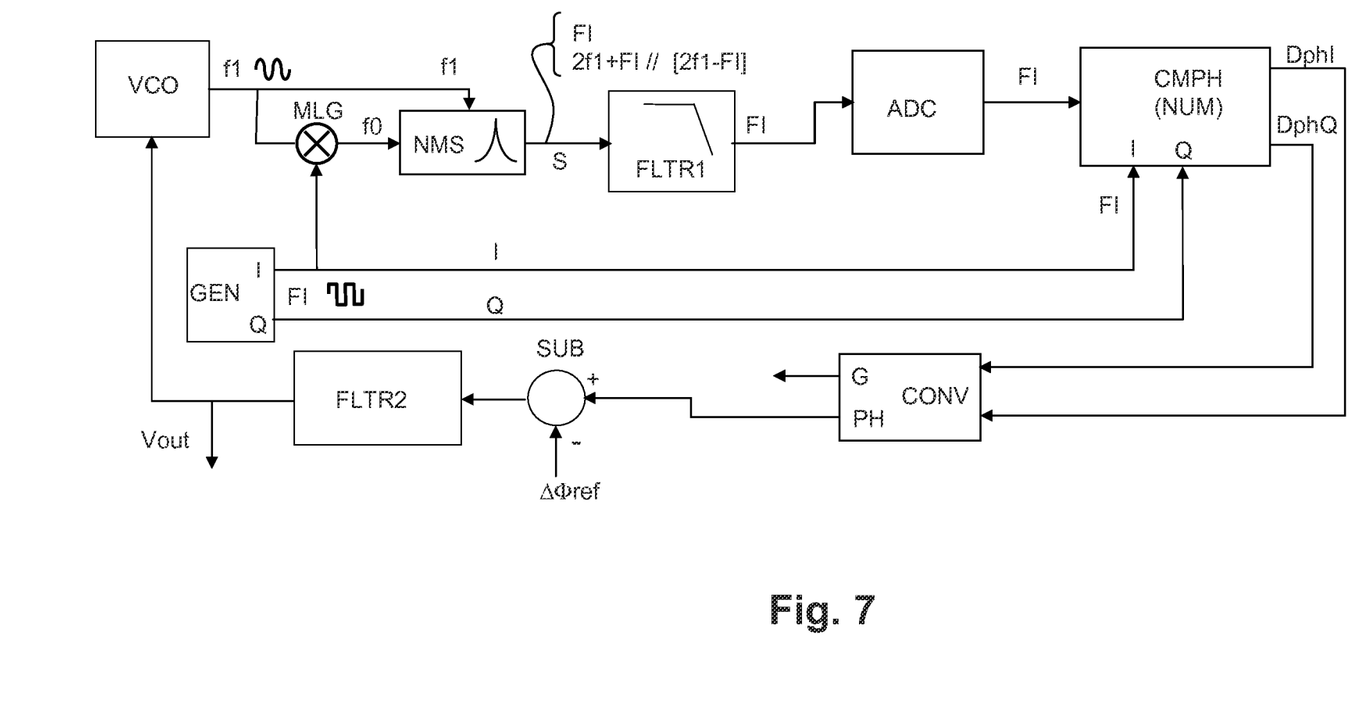
FIG. 7 represents a measurement circuit in which the phase comparator works on two paths in phase quadrature.

FIG. 7 represents a preferred embodiment in which the generator GEN supplies two signals at frequency FI in phase quadrature, and the phase comparator CMPH (preferably digital) processes these two paths to supply two phase shift measurement signals DphI and DphQ. Their quadratic sum depends on the amplitude of the detected signal, and their ratio represents the phase of the detected signal.

In this case, the generator GEN preferably supplies two square signals in phase quadrature to the phase comparator. If it supplies sinusoidal signals to the mixer MLG, these signals are supplied for example after conversion in a digital-to-analogue converter forming part of the generator, and the square signals that are sent to the phase comparator are then read upstream of this converter rather than downstream. But if the signals sent to the mixer MLG and to the phase comparator are square, the generator can then be a simple logic circuit controlled by a clock with a frequency the quadruple of FI.

The digital signals DphI and DphQ representing the phase shift (measurements in Cartesian coordinates), are converted into a gain G and a phase shift PH (measurements in polar coordinates) by a computing member CONV. The gain is the quadratic sum of the phase shifts DphI and DphQ; the phase is the arctangent of the ratio DphQ/DphI. The gain G is only used during the open-loop calibration serving to determine the phase shift at resonance; indeed, it is the gain peak that defines the resonance. In the open loop, the phase PH takes at resonance the value Δϕref that will be applied as setpoint in the closed loop. In the closed loop, the phase PH is applied to the subtractor SUB.

Figure 8:
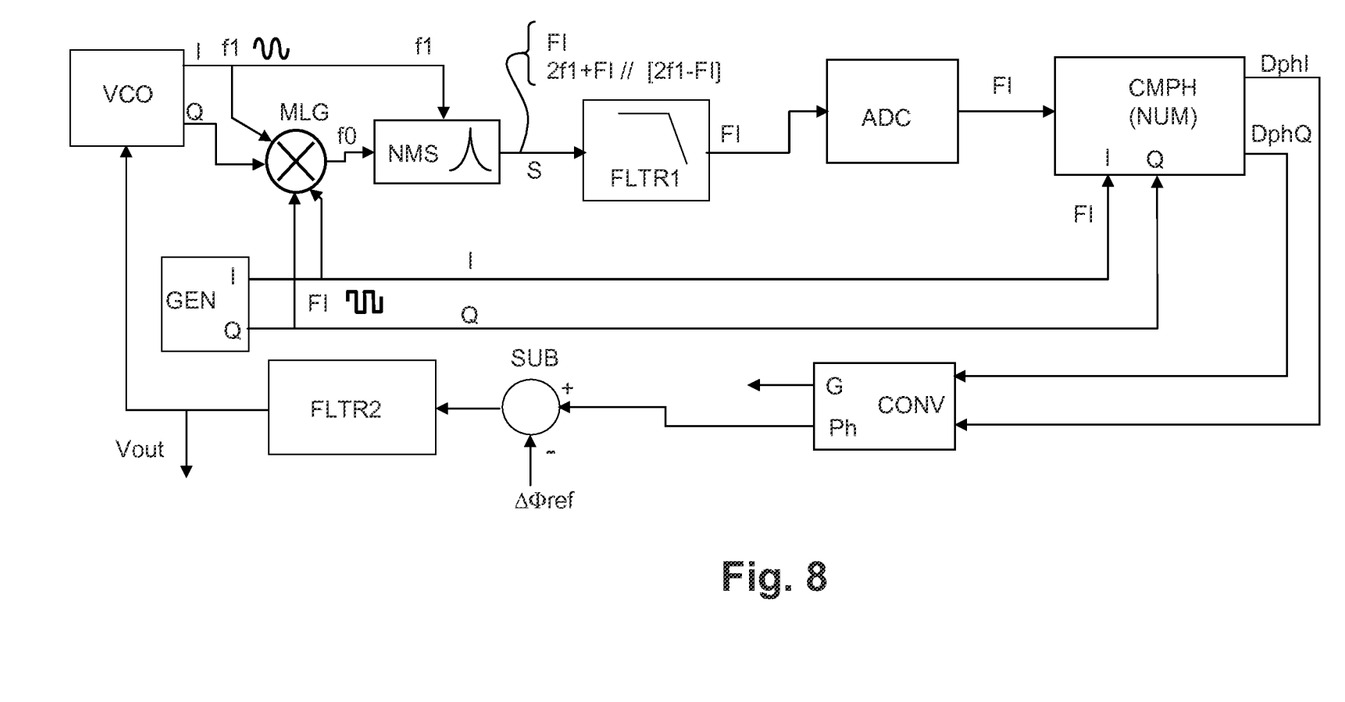
FIG. 8 represents a measurement circuit in which the polarization frequency is produced on two paths in phase quadrature to be mixed with the intermediate frequency also produced on two paths in phase quadrature.

FIG. 8 represents an embodiment in which the frequency-controlled oscillator VCO itself also provides two paths in phase quadrature. This is possible notably if the oscillator is produced by a direct frequency digital synthesis circuit with a variable frequency comprising a digital-to-analogue converter.

In this case the two paths I and Q output by the oscillator VCO, and the two paths I and Q output by the generator GEN can be applied to the mixer MLG. The latter is then a complex mixer and not a simple mixer. It includes four input paths and two outputs. However, a single output is used in closed loop. The advantage of a complex mixer, which mixes the paths I and Q at the same time, is the fact that the outputs can supply either the sum frequency or the difference frequency, instead of these two frequencies being mixed in one and the same output. This notably facilitates open-loop calibration, because one knows whether one is centred on the sum frequency or on the difference frequency. But in the closed loop it is possible to reconfigure the complex mixer into a simple mixer, enabling a reduction in phase noise. The reconfiguration is carried out by swapping the inputs and outputs.

Figure 9:
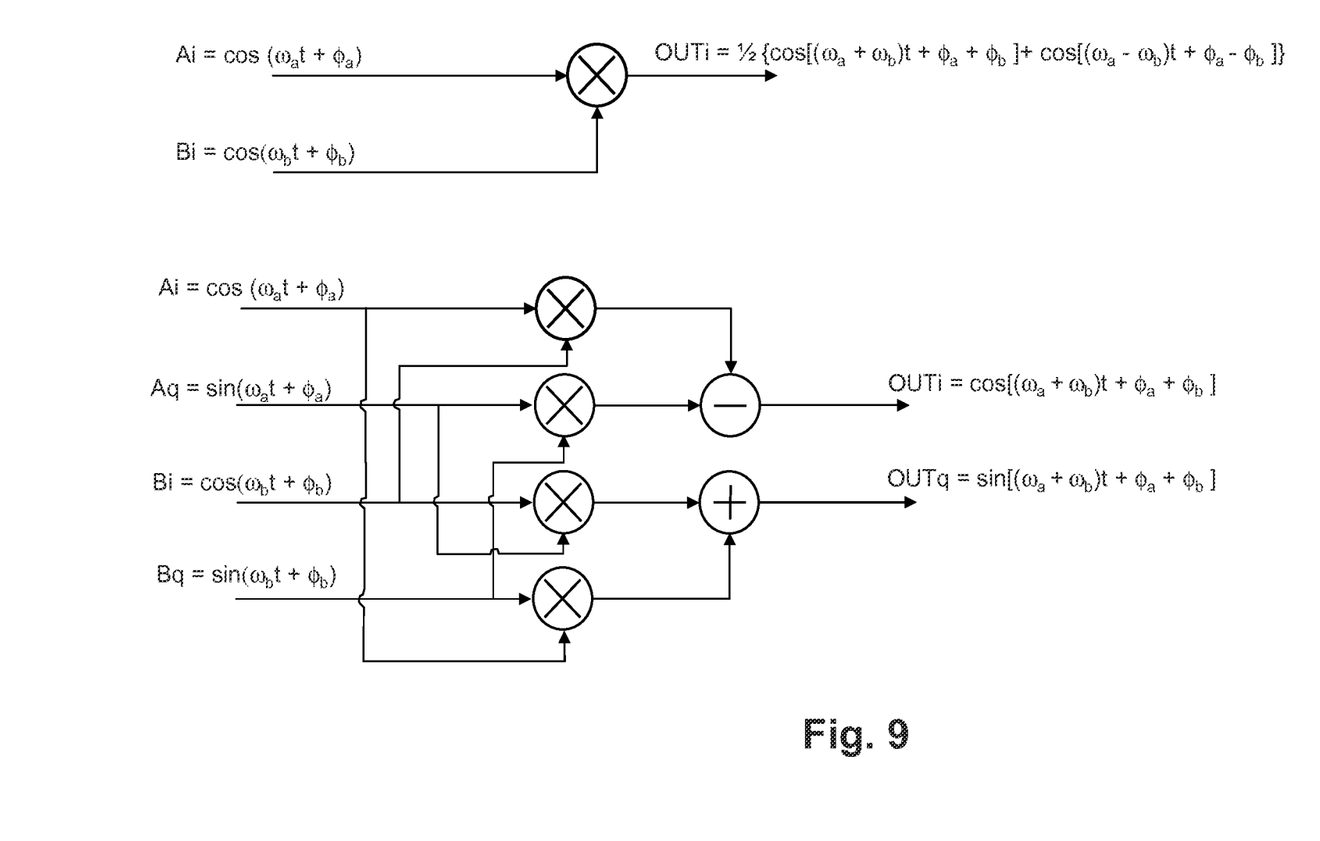
FIG. 9 represents the design and equations governing a simple mixer and a complex mixer.

FIG. 9 represents the principle of a complex mixer, compared to a simple mixer. The general equations governing the mix are the following, in which Ai and Bi represent two input signals of frequencies $\omega_a$ and $\omega_b$ respectively and phases $\phi_a$ and $\phi_b$ respectively, Aq and Bq represent the corresponding signals in phase quadrature with the former, OUTi represents the output in the case of a simple mixer of Ai and Bi, and OUTi and OUTq represent the two outputs in phase quadrature in the case of a complex mixer. The amplitudes of the input signals are normalized to 1.

1) Simple Mixer of Ai and Bi:

It comprises only a multiplier receiving the signals Ai and Bi.

$$Ai = \cos(\omega_a t + \phi_a)$$

$$Bi = \sin(\omega_b t + \phi_b)$$

$$OUTi = \tfrac{1}{2}\{\cos[(\omega_a + \omega_b)t + \phi_a + \phi_b] + \cos[(\omega_a - \omega_b)t + \phi_a - \phi_b]\}$$

Both the sum and difference frequency components are present simultaneously in the output.

2) Complex Mixer of Ai, Bi, Aq and Bq

It comprises four multipliers to produce the products AiBi, AqBq, AiBq and AqBi, and two adders to produce the quantities (AiBi−AqBq) and (AqBi+AiBq).

$$Ai = \cos(\omega_a t + \phi_a)$$

$$Bi = \cos(\omega_b t + \phi_b)$$

$$Aq = \sin(\omega_a t + \phi_a)$$

$$Bq = \sin(\omega_b t + \phi_b)$$

$$OUTi = (AiBi - AqBq) = \cos[(\omega_a + \omega_b)t + \phi_a + \phi_b]$$

$$OUTq = (AqBi + AiBq) = \sin[(\omega_a + \omega_b)t + \phi_a + \phi_b]$$

The sum frequency $(\omega_a + \omega_b)$ alone appears in the output signals; but it is possible to obtain the difference frequency $(\omega_a - \omega_b)$ alone by crossing the connections between multipliers and adders in a different way.

The complex mixer can be reconfigured as a simple mixer by not using the adders and by only using the first multiplier receiving Ai and Bi.

Figure 10:
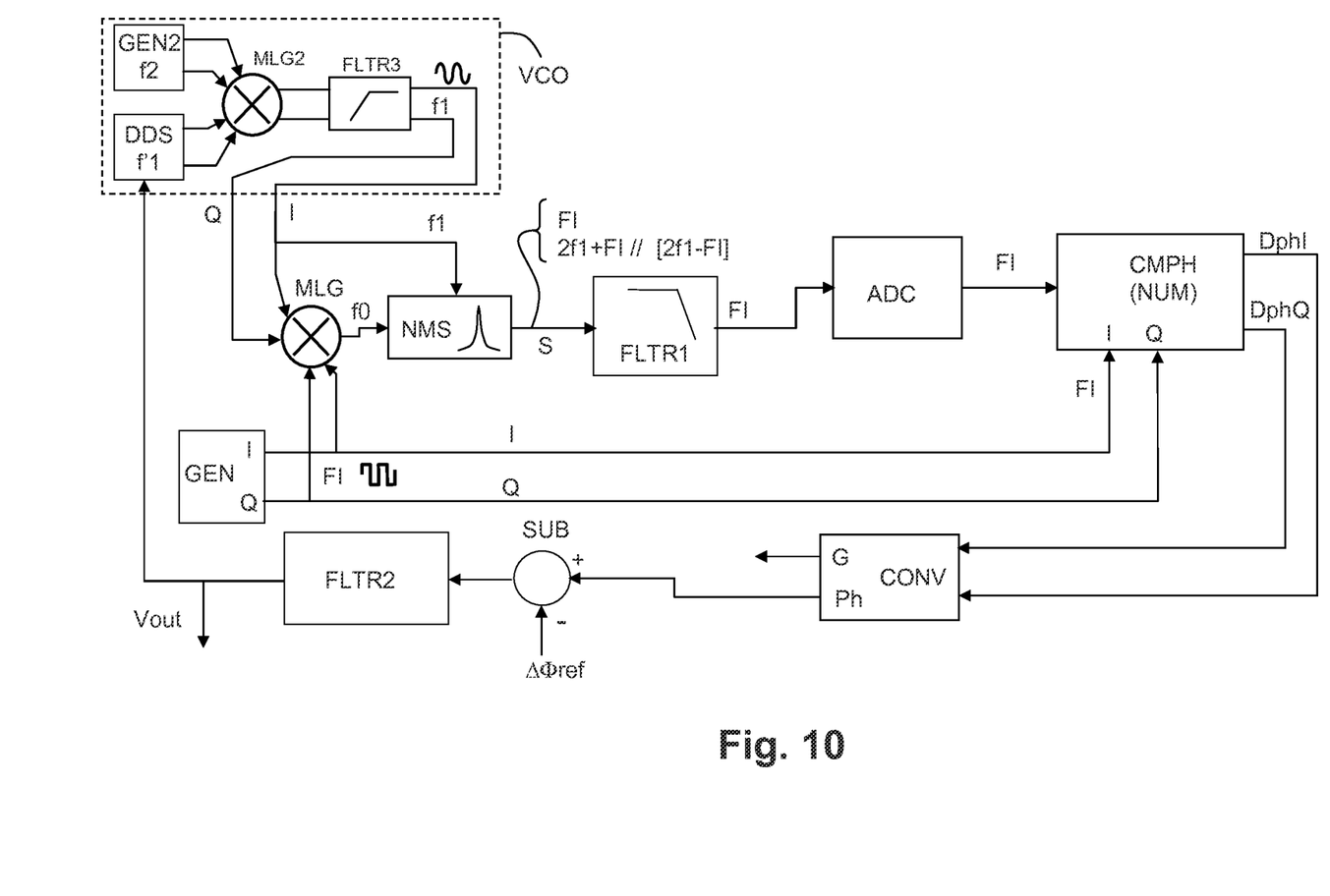
FIG. 10 represents a measurement circuit in which the polarization frequency is itself produced by mixing a (configurable) fixed frequency and a frequency controlled by the locked loop.

FIG. 10 represents a particular embodiment in which the frequency-controlled oscillator that produces the polarization frequency f1 is composed of several parts: an analogue or digital frequency-controlled oscillator DDS operating at a lower frequency f'1 and controlled by the locked loop, an oscillator GEN2 at a fixed but configurable frequency f2, a mixer MLG2 for mixing the frequency f'1 and the frequency f2 to produce the sum frequency and the difference frequency and a filter FLTR3 for eliminating one of these two frequencies, for example f2−f'1, and preserving the other one f2+f'1 as the polarization frequency f1.

This makes it possible to simplify the embodiment of the oscillator controlled by the loop, in particular when the latter is composed of a direct digital frequency synthesizer followed by a digital-to-analogue converter; indeed, this converter can then be made to work at a fairly low frequency f'1 and over a limited range of variation. This also makes it possible to work with resonators of various frequencies, by adjusting the value of the offset frequency f2 as a function of the type of resonator used, without operating on the intermediate frequency FI.

The oscillator at frequency f'1 controlled by the locked loop can be a direct digital frequency synthesizer supplying two signals in phase quadrature. The configurable fixed-frequency oscillator f2 can be a simple clock circuit supplying two square signals in phase quadrature (which is particularly simple to produce), or a digital synthesizer, more complex but supplying sinusoidal signals, and therefore of better spectral purity.

The adjustment of the frequency f2 is carried out as a function of the range of resonators used. In fact, by supposing that the intermediate frequency FI is fixed, the range of resonant frequencies f0 varies as a function of the characteristics of the resonator; the range of polarization frequencies f1 varies in the same way; but the variation range of f1 can be very limited if the frequency f2 is chosen appropriately by taking account of the range of resonant frequencies in which the resonator under consideration is situated; it is therefore possible to make do with a simple controlled-frequency oscillator not requiring a large range of variation in its frequency to provide the lock.

The invention claimed is:

1. A measurement circuit for measuring the oscillation frequency of a resonator, said circuit including an excitation input for receiving an actuation signal at a frequency close to a resonant frequency of the resonator and a polarization input for receiving a polarization signal comprising an AC component at a polarization frequency f1, the circuit including a phase-locked loop comprising the resonator, a frequency-controlled oscillator, and a phase comparator, wherein said polarisation frequency is applied by the frequency-controlled oscillator to said polarization input of the resonator, and wherein the circuit furthermore comprises a frequency generator supplying a fixed intermediate frequency FI, a mixer for mixing the intermediate frequency and the polarization frequency f1 and having an output for supplying an excitation frequency f0 that is the sum or difference of f1 and FI and for applying this excitation frequency f0 to the excitation input as actuation signal, the phase comparator receiving the intermediate frequency FI from the generator and a filtered output signal coming from the resonator, and supplying a locking signal to the frequency-controlled oscillator for controlling the polarization frequency f1 of the oscillator in a direction tending to maintain the excitation frequency at the output of the mixer at the value of the resonant frequency of the resonator.

2. A measurement circuit according to claim 1, wherein the intermediate frequency FI has a value greater than a bandwidth of the resonator.

3. A measurement circuit according to claim 1, wherein the output of the mixer is applied directly to the excitation input of the resonator, without prior high-pass filtering.

4. A measurement circuit according to claim 1, wherein the frequency generator that produces the intermediate frequency FI supplies a sinusoidal signal or a square signal.

5. A measurement circuit according to claim 4, wherein the frequency generator is a clock circuit supplying a square signal at the frequency FI.

6. A measurement circuit according to claim 1, wherein the frequency generator supplies two signals in phase quadrature.

7. A measurement circuit according to claim 6, wherein the frequency-controlled oscillator supplies two signals in phase quadrature.

8. A measurement circuit according to claim 7, wherein the mixer is a complex mixer receiving the phase quadrature signals of the frequency-controlled oscillator as well as those of the frequency generator and producing on an output a sum or difference frequency of the received frequencies.

9. A measurement circuit according to claim 8, wherein the complex mixer is used as a complex mixer in an open-loop calibration phase and as a simple mixer, supplying at once a sum frequency and a difference frequency on its output, in a closed-loop use phase.

10. Measurement circuit according to claim 1, wherein the frequency-controlled oscillator comprises analogue or digital means for establishing a variable frequency f'1 under the control of the phase-locked loop, and a mixer for mixing this frequency f'1 with a fixed frequency f2 and thus producing the polarization frequency f1.

11. A measurement circuit according to claim 2, wherein the output of the mixer is applied directly to the excitation input of the resonator, without prior high-pass filtering.

12. A measurement circuit according to claim 2, wherein the frequency generator that produces the intermediate frequency FI supplies a sinusoidal signal or a square signal.

13. A measurement circuit according to claim 3, wherein the frequency generator that produces the intermediate frequency FI supplies a sinusoidal signal or a square signal.

14. A measurement circuit according to claim 11, wherein the frequency generator that produces the intermediate frequency FI supplies a sinusoidal signal or a square signal.

15. A measurement circuit according to claim 12, wherein the frequency generator is a clock circuit supplying a square signal at the frequency FI.

16. A measurement circuit according to claim 2, wherein the frequency generator supplies two signals in phase quadrature.

17. A measurement circuit according to claim 3, wherein the frequency generator supplies two signals in phase quadrature.

18. A measurement circuit according to claim 2, wherein the frequency-controlled oscillator comprises analogue or digital means for establishing a variable frequency f'1 under the control of the phase-locked loop, and a mixer for mixing this frequency f'1 with a fixed frequency f2 and thus producing the polarization frequency f1.

19. A measurement circuit according to claim 3, wherein the frequency-controlled oscillator comprises analogue or digital means for establishing a variable frequency f'1 under the control of the phase-locked loop, and a mixer for mixing this frequency f'1 with a fixed frequency f2 and thus producing the polarization frequency f1.

* * * * *